(12) United States Patent
Worley et al.

(10) Patent No.: US 7,462,184 B2
(45) Date of Patent: Dec. 9, 2008

(54) INTRODUCER FOR ACCESSING THE CORONARY SINUS OF A HEART

(75) Inventors: Seth J. Worley, Lancaster, PA (US); Paul Kurth, Rancho Palos Verdes, CA (US)

(73) Assignee: Pressure Products Medical Supplies Inc., Santa Barbara, CA (US)

( * ) Notice: Subject to any disclaimer, the term of this patent is extended or adjusted under 35 U.S.C. 154(b) by 372 days.

(21) Appl. No.: 10/139,551

(22) Filed: May 6, 2002

(65) Prior Publication Data

US 2003/0208141 A1 Nov. 6, 2003

(51) Int. Cl.
*A61B 19/00* (2006.01)
*A61M 25/00* (2006.01)

(52) U.S. Cl. ....................... 606/129; 604/532

(58) Field of Classification Search ............ 606/191, 606/194, 129, 108, 192; 604/264, 523, 525, 604/528, 532

See application file for complete search history.

(56) References Cited

U.S. PATENT DOCUMENTS

| | | | | |
|---|---|---|---|---|
| 5,584,803 A | * | 12/1996 | Stevens et al. | 604/6.16 |
| 5,643,231 A | * | 7/1997 | Lurie et al. | 604/532 |
| 5,722,963 A | * | 3/1998 | Lurie et al. | 604/525 |
| 5,766,151 A | * | 6/1998 | Valley et al. | 606/194 |
| 5,814,016 A | * | 9/1998 | Valley et al. | 604/96.01 |
| 5,868,702 A | * | 2/1999 | Stevens et al. | 604/96.01 |
| 5,952,471 A | * | 9/1999 | Griffiths Lawson | 530/387.1 |
| 5,957,911 A | * | 9/1999 | Nesto | 604/532 |
| 6,001,085 A | * | 12/1999 | Lurie et al. | 604/524 |
| 6,002,955 A | * | 12/1999 | Willems et al. | 600/374 |
| 6,110,163 A | * | 8/2000 | Voda | 604/523 |
| 6,203,531 B1 | | 3/2001 | Ockuly et al. | |
| 6,273,881 B1 | * | 8/2001 | Kiemeneij | 604/532 |
| 6,277,107 B1 | * | 8/2001 | Lurie et al. | 604/528 |
| 6,458,107 B1 | * | 10/2002 | Ockuly | 604/523 |
| 6,595,983 B2 | * | 7/2003 | Voda | 604/530 |

* cited by examiner

*Primary Examiner*—Julian W Woo
(74) *Attorney, Agent, or Firm*—Daniel L. Dawes (57) ABSTRACT

The invention is defined as a precurved coronary sinus guiding introducer for use in a cardiomyopathic heart comprising a flexible elongated member with a proximal and distal end. The elongated member comprises a generally straight, proximal portion and a precurved distal portion. In one embodiment the proximal portion and distal portion are formed to lie is a common plane. In another embodiment the portions are angulated with respect to each other in different planes. The precurved distal portion comprises at least one curved subportion and at least one curved or straight subportion. The precurved distal subportion curves through a generally circular arc away and is defined by a chord of predetermined length. The precurved distal subportion has a predetermined height above the chord. The curved or straight subportion is the distal section of the precurved distal portion.

78 Claims, 7 Drawing Sheets

INTRODUCER FOR ACCESSING THE CORONARY SINUS OF A HEART

BACKGROUND OF THE INVENTION

1. Field of the Invention

This invention relates to sheaths and introducers, which are utilized in a human heart, which has been altered by heart disease. More particularly, this invention relates to a precurved, guiding introducer for introducing specialized medical devices into the coronary sinus of a heart with cardiomyopathy and a process for introduction of those devices into the coronary sinus utilizing the precurved, guiding introducer.

2. Description of the Prior Art

Many medical procedures require the introduction of specialized medical devices into the human heart. For example, electrical leads, such as pacemaker leads, defibrillation leads or leads used for cardioversion, or specialized catheters are frequently placed at specific locations within the heart to perform specialized cardiac procedures. Many of these medical devices, such as pacemaker leads, are very pliant and flexible. This flexibility is necessary to prevent damage, particularly to the patient's vasculature, during the period of time those products are present in the patient. However, because of this flexibility, it is quite difficult to advance these devices through the patient's vasculature into the heart without the use of some stiffening element with the device. For example, one method of stiffening certain medical devices is to introduce a stylet into the lumen of the medical device.

The typical procedure for introducing these devices into the heart requires passage through the patient's vasculature. One early approach to introduction of devices into the vasculature was to surgically cut an opening into the patient's vasculature. However, there are several disadvantages to this procedure. To address these disadvantages, percutaneous methods have been developed to create openings in the vasculature. Once an opening is created, frequently by use of a hollow needle, a dilator is usually inserted into the vasculature, which gradually increases the size of the opening. The dilator has a tapered end, which spreads apart the tissue at the puncture sight as it is advanced through the vasculature. Often the dilator will contain a lumen through which other medical devices may also be inserted into the vasculature.

As an example, in a typical procedure for introduction of an electrode lead into the heart, a guidewire is first introduced through the vasculature into the appropriate chamber of the heart. With the guidewire in place, a catheter/introducer or dilator/introducer combination is then passed over the guidewire and directed into the patient's body. The catheter or dilator is then removed from the introducer. The introducer then provides a platform from which the lead may be introduced into the heart, frequently with a stylet placed within the lumen of the lead to assist in stiffening the structure of the lead and also to permit precise placement of the device within the heart.

With conventional introducers, the maximum diameter of the pacemaker lead that can be inserted is no larger than the lumen of the introducer. This limitation created a significant problem because of the nature of pacemaker leads. Frequently, the pacemaker lead's proximal end contained an electrical connector for connection to the pulse generator. Because the size of the connecter is often larger than the diameter of the lumen of conventional cardiac introducers or sheaths, the invention contemplates that these introducers or sheaths are splittable, sliceable or tearable to assist in the insertion of these electrode leads. Once the introducer directs the placement of the medical device, such as an electrode lead, into the body, the splittable, sliceable or tearable introducer is separated lengthwise as it is withdrawn from the body. By being separable by some means, the size of the lumen of the splittable, sliceable or tearable introducer can remain relatively small as it need be no larger than is necessary for passage of the distal tip of the medical device through the lumen of the introducer. In addition, the prior art uses a splittable hemostatic valve, such as shown in U.S. Pat. Nos. 5,125,904 and 5,312,355, that is utilized in combination with a splittable sheath for introduction of a pacemaker electrode into a patient.

While specialized medical devices are utilized throughout the human body, many have been used in the heart, in general and specifically in the coronary sinus. The coronary sinus is the largest cardiac vein in the heart and serves as a venous conduit from smaller veins within the myocardium to the right atrium. A tissue fold or primitive valve covers the coronary sinus ostium to prevent blood from backflowing into the coronary sinus as it is being pumped out of the right atrium. Located within the right atrium, generally, above the coronary sinus is an oval depression called the fossa ovalis. Between the inferior vena cava and the coronary sinus ostium is the Eustachian ridge. The location of each of these elements may vary from patient to patient.

The coronary sinus is often used for electrophysiological procedures in the heart, including both diagnostic and treatment procedures. The coronary sinus can also be used as a location for pacing both the left and right sides of the heart. Gaining access to the ostium of the coronary sinus is a very difficult procedure, especially because of the large number of similar anatomical structures located near the coronary sinus within the right atrium. It is especially difficult because these anatomical structures do not show up on a fluoroscope.

Current procedures available for introduction of devices such as pacemaker leads, implantable defibrillator leads, specialized catheters or devices used for cardioversion into the coronary sinus are frequently time consuming and difficult. To address this problem for a particular type of diagnostic catheter, various researchers have devised precurved, coronary sinus catheters, which because of their curvature, can be advanced through the patient's vasculature directly into the coronary sinus, where it can be used for diagnostic and treatment procedures such as disclosed in U.S. Pat. No. 6,277,107.

While several preshaped or biased introducers have been proposed, the shapes provided are still difficult to manipulate successfully and quickly into the coronary sinus. It typically takes a considerable amount to time and physician skill to manipulate these shaped introducers successfully into the opening of the coronary sinus.

The presence, diameter, angulation, and tortuosity of veins as may be visualized by retrograde venography determine their acceptability for the placement of a lead in a predetermined location. Despite the considerable variability of the coronary venous system among patients, in one study a lateral vessel for lead introduction was available in 82%, and a posterior or lateral vessel was available in 99% of individuals within a patient population that could potentially benefit from a lead on the left ventricle. Similar variations in anatomic location are present in the coronary sinus os. See Eckhard Meisel, MD et. al., *"Investigation of Coronary Venous Anatomy by Retrograde Venography in Patients With Malignant Ventricular Tachycardia"*, Circulation, 2001; 104:442.

Accordingly, it is an aspect of this invention to disclose an optimally shaped device, which assists in the efficient placement of medical devices particularly small, flexible medical devices, such as electrode leads, into the coronary sinus, even by physicians without a high level of experience in using the device.

It is a further aspect of this invention to disclose an introducer for use by ordinarily skilled physicians without specific experience with the introducer to allow a medical device, such as a flexible lead for use with a pacemaker, defibrillator or for cardioversion, to be introduced into the coronary sinus.

Another aspect of this invention is to disclose a fixed shape introducer to be used for the introduction of medical devices into the coronary sinus by ordinarily skilled physicians without specific experience with the introducer.

Another aspect of the invention is to disclose a fixed shaped introducer which can be used in a process for the introduction of medical devices into the coronary sinus without using a guidewire by ordinarily skilled physicians without specific experience with the introducer.

Another aspect of the invention is to disclose a process for the introduction of flexible medical devices into the coronary sinus of the human heart using a precurved guiding introducer by ordinarily skilled physicians without specific experience with the introducer.

These and other aspects are obtained by the design of the device of the present invention and by the process disclosed herein.

BRIEF SUMMARY OF THE INVENTION

The invention is primarily used in diseased hearts, namely enlarged hearts having cardiomyopathy. The invention is defined as a precurved coronary sinus guiding introducer comprising a flexible elongated member with a proximal and distal end. The elongated member comprises a generally straight, proximal portion and a precurved distal portion. In the illustrated embodiment the proximal portion and distal portion are formed to lie is a common plane. However, it must be understood that the curved subportion and the straight subportion of the the common plane by plus or minus 30-40 degrees. The precurved distal portion comprises at least one curved subportion and at least one curved or straight subportion. The precurved distal subportion curves through a generally circular arc away and is defined by a chord of predetermined length. The precurved distal subportion has a predetermined height above the chord. The curved or straight subportion is the distal section of the precurved distal portion. The distal most section of the precurved distal portion is generally oriented in a direction parallel to the straight, proximal portion or is oriented to extend in a direction approximating the general direction of the proximal portion.

In one embodiment the coronary sinus guiding introducer further comprises a lumen extending through the member from the proximal to the distal end. In another embodiment the member is solid and is used as a dilator for use in combination with a catheter.

In the illustrated embodiment the chord has the predetermined length of approximately 6-18 cm (2.5 to 7 inches) and the predetermined height above the chord is approximately 6-10 cm (2.5 inches to 4.0 inches).

More particularly, the chord has the predetermined length of approximately 14 cm (5.5 inches) and the predetermined height above the chord is approximately 6.3 cm (2.5 inches). The curved or straight subportion is approximately 1.2 to 11.5 cm (0.5 to 4.5 inches) in length and preferably approximately 6.3 cm (2.5 inches) in length. The member has an inside diameter of 9 French.

In one embodiment, the pre-curved distal portion has a maximal length of approximately 16 in.; the chord has a length of approximately 4.6-7 in.; the height of the chord is at least 2.65 in or at least 1.5 in.; the length of the curved or straight distal sub-portion is 0.7-1.6 in.; the length of the pre-curved distal portion is approximately 7.2 in.; or the length of the pre-curved distal portion being 7.2 in.-16 in.

In one embodiment the invention is a precurved coronary sinus guiding introducer for use in a heart comprising a flexible elongated member with a proximal and distal end. The elongated member comprises a generally straight, proximal portion and a precurved distal portion. The proximal portion and distal portion is formed to lie in a common plane. The precurved distal portion comprises at least one curved subportion and at least one curved or straight subportion. The precurved distal subportion curves through a generally circular arc defined by a chord of predetermined length and the precurved distal subportion has a predetermined height from the chord. The curved or straight subportion is the distal section of the precurved distal portion.

In one embodiment the precurved distal subportion is comprised of two curved portions and two straight portions in alternating sequence with a distal one of the two straight portions leading to the distal end.

In another embodiment the two curved portions comprise a proximal curved portion having a radius of curvature of approximately 2.0±0.25 to 2.85 ±0.25 inches and a distal curved portion having a radius of curvature of approximately 1.25 ±0.25 to 2.0±0.25 inches.

In still another embodiment the precurved distal subportion is further comprised of three curved portions and the curved or straight portion leading to the distal end. The three curved portions each have a different radius of curvature with the portion having the largest radius of curvature being between the other two curved portions.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

The coronary sinus guiding introducer of the present invention assists an ordinarily skilled and experienced physician or cardiologist, having no special prior experience with the introducer of the invention, in the quick introduction of specialized medical devices, such as a pacemaker lead or defibrillator lead, into the coronary sinus of the human heart.

The coronary sinus is the largest cardiac vein and serves as a conduit for access to various locations within the heart. Depending on the depth of insertion of the medical device into the coronary sinus, both the left and right atria and the left and right ventricles of the heart can be analyzed. However, introduction of a medical device into the ostium of the coronary sinus is quite difficult as a result of the structure of the heart, the difficulty in locating the coronary sinus using conventional medical technology and the constantly changing shape of the heart while beating as well as the altered anatomy of the heart with cardiomyopathy. Because of its unique shape, the introducer of the present invention assists in rapid placement of medical devices within the coronary sinus, thereby reducing the amount of time necessary for performance of the medical procedure. (The term "introducer" is synonymous with the term "sheath.")

Two approaches are commonly used for placement of a medical device within the coronary sinus, an inferior approach from below the heart, and a superior approach from above the heart. In the superior approach, the device is advanced through either the left cephalic or left subclavian vein through the superior vena cava into the right atrium until it is directed toward the coronary sinus. See FIG. 1a. In the inferior approach, the device is generally advanced through the femoral vein through the inferior vena cava into the right atrium. See FIG. 1b. The tip of the device is then directed toward the ostium of the coronary sinus. The superior approach is the preferred approach and is the approach for which the introducer of the present invention is optimized.

Medical practitioners often monitor the introduction of medical devices and their progress through the vascular system by use of fluoroscopes. Unfortunately, fluoroscopes cannot easily identify specific features in the heart, in general, and the critically important structures of the right atrium, specifically, thus making placement of medical devices into the coronary sinus extremely difficult. In addition, placement of medical devices in the coronary sinus is especially difficult when the heart is beating and the location of the coronary sinus altered by cadriomyopathy. In particular, when the medical device to be introduced is a flexible, flaccid product such as a pacemaker lead, placement in the coronary sinus is especially difficult.

In this case the introducer is designed to be used in diseased hearts, or having cardiomyopathy, which hearts have been enlarged because of that disease. Because of the enlargement of the hearts the anatomy is changed and shapes which have been designed for normal hearts or hearts having other diseases other than cardiomyopathy are difficult to use. The claimed design is surprisingly adapted to quick and easy access to the coronary sinus in cardiomyopathic hearts.

The structure and shape of the guiding introducer of the present invention addresses and solves this problem and permits the precise and quick placement necessary for introduction of medical devices, such as leads, into the coronary sinus even by those physicians not having extensive prior experience with the introducer. The shaped guiding introducer of this invention readily positions the medical device inserted through its lumen at the precise location necessary for the procedure as a result of its shape.

This specially designed guiding introducer is generally produced from a conventional elongated introducer. The guiding introducer of the invention is produced utilizing a conventional introducer production procedure and is preferably formed as a single, unitary structure.

Figure 2:
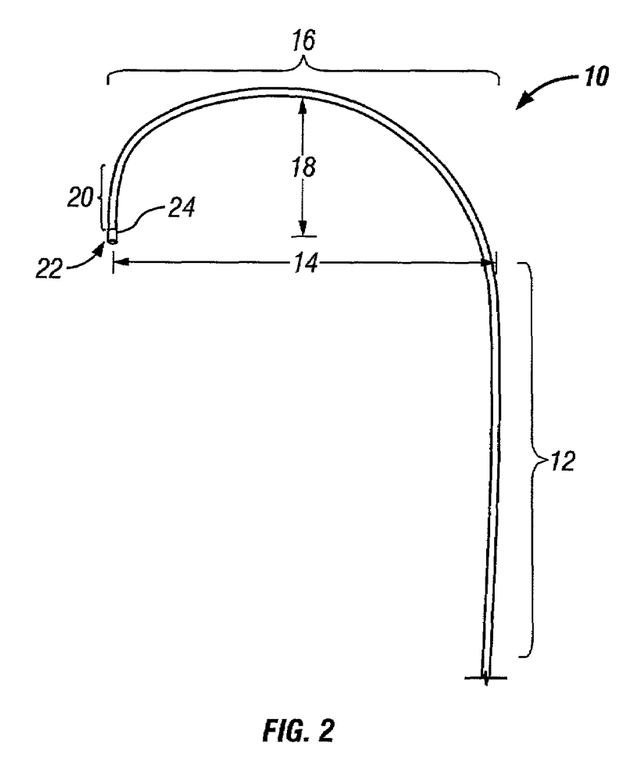
FIG. 2 is side view of an introducer formed according to the invention, which is placed in the coronary sinus using the superior approach and where various portions of the introducer lie in a single plane.

FIG. 2 is a plan elevational side view of introducer 10 of the invention. Introducer 10 lies in a single plane, such as the plane of FIG. 2. Portion 12 is the defined as the proximal portion of introducer 10 and is a generally unbiased, flexible section of introducer 10 leading from the percutaneous introduction point into the left auxiliary subclavian vein and through the vasculature leading toward the atrium of the heart.

A biased portion 16 of introducer 10 forms the distal portion of introducer 10, and is either integral with or may be separately fabricated from portion 12. While still being flexible, portion 16 is biased to have a memory so that when the vasculature permits, it tends to assume a prebiased shape as seen in FIG. 2 and described in more detail below. On the other hand, the bias is not so strong that portion 16 is not easily conformed to the vasculature without risk of injury.

In general terms, as shown in FIG. 2 portion 16 has an arcuate bias to form a modified circular curvature so that the chord 14 is defined in a direction perpendicular to proximal portion 12 as shown in the drawing across the open mouth of the hook shape or arc from where the arc beings and is in one embodiment approximately 14cm (5.5inches) in a sheath or introducer 10 having a total length of 45cm and a 9French diameter. However, the chord length 14 may vary within a range of the illustrated embodiment, namely in a range of 6-18cm (3.5to 7inches). As shown in FIG. 2, the height 18 of the chord above portion 16 of the arc is defined in a direction perpendicular to chord 14 as shown in the drawing and is approximately 6cm (2.5inches) in the illustrated embodiment, but may range from 3.8to 10.2cm (1.5to 4.0inches).

The distal-most end portion 20 of portion 16 is straightened or slightly straightened to at least have less curvature than the remainder of portion 16 or a very low curvature, if any. Portion 20 has a length of approximately 2.5 cm (1 inch), but again may vary in a range of approximately 1.2 to 11.5 cm (0.5 to 4.5 inches).

The guiding introducer 10 may be made of any biocompatible material suitable for use in humans which has a memory or permits distortion from and substantial return to the desired three dimensional shape, such as polyethylene or polyurethane. As is conventional the distal tip 22 of the guiding introducer 10 may be made of a more pliable, more compressible material, than the remaining length of the coronary sinus guiding introducer 10 to prevent damage to the vasculature and the coronary sinus when in use. Also, preferably, the distal tip 22 is made radioopaque by use of a marker 24.

For the purpose of illustration and not limitation, the internal diameter of the guiding introducer 10 may vary from about 4 to about 16 French (1 French equals ⅓ of a millimeter). Such guiding introducers 10 can thus accept dilators whose outside diameter is from about 4 to about 16 French. Obviously, if larger or smaller dilators or other medical devices are used in combination with the guiding introducer, modifications in size and shape of the guiding introducer 10 can be made. The precurved guiding introducer 10 of the invention may also be multi-lumened. According to conventional design principles, the structure of the introducers 10 may be modified to permit the presence of an inflatable balloon near or at its distal tip or electrodes for sensing or ablation.

Variations in size and shape of the guiding introducer 10 are intended to encompass pediatric uses for the guiding introducer of the present invention, although the preferred uses are in adult human hearts. It is well recognized that pediatric uses may require reductions in size of the various portions of the guiding introducer 10, in particular shortening the first portion 12, with a proportional reduction in the height, arc and length of the distal portion 16 of the guiding introducer 10, which may extend the lower limits of the specific ranges of the above parameters from those explicitly recited above. In addition, variations in size or shape are also intended to encompass specialized situations that sometimes occur in patients with enlarged or rotated hearts.

The structure of the guiding introducer 10 should be stiff enough to prevent substantial movement of the distal section of the guiding introducer 10 once in place within the heart and to retain its general shape. According to conventional design principles, in order to permit good torque control, the generally straight portion 12 may be made stiffer than the curved distal portion 16. This stiffer construction can be achieved by conventional construction techniques, such as increasing the thickness of the material or manufacturing a portion of the guiding introducer 10 from a material possessing characteristics of enhanced stiffness, such as by adding a metal component, a stiffener material or by fusing different materials together.

The second, distal portion 16 of the guiding introducer should be stiff, but flexible. This will permit the curved section of distal portion 16 to be straightened when a dilator is passed through its lumen to facilitate insertion into the patient's vasculature and for passage through the vasculature into the right atrium. The distal tip portion 20 should be more pliable than the remaining portions of the guiding introducer 10 to prevent damage to the vasculature during insertion of the guiding introducer through the vasculature.

As is well known the stiffness of the coronary sinus guiding introducer 10 can also be enhanced by insertion of a dilator or shaped catheter within the lumen of the guiding introducer 10. A "dilator" is an inner strengthening element intended to be removed to allow placement of the introducer 10. The dilator acts as a stiffening means for stiffening the structure of the coronary sinus guiding introducer 10. The dilator is produced from conventional dilator material and preferably contains a lumen passing therethrough for use with a guidewire. The shape of the dilator conforms to the shape of the coronary sinus guiding introducer 10. By using a dilator with the same shape as the coronary sinus guiding introducer 10, upon insertion of the dilator into the coronary sinus guiding introducer 10, support for the overall shape of the coronary sinus guiding introducer 10 is enhanced. By use of these complementary shapes, smooth and effective placement of the coronary sinus guiding introducer 10 into the coronary sinus is possible.

If desired the shape of the dilator can be straight, such that upon introduction into the lumen of any of the precurved coronary sinus guiding introducer 10 discussed above, the overall shape of the coronary sinus guiding introducer 10 is straightened, making insertion of the combination through the vasculature easier. When the dilator is removed from the lumen of the coronary sinus guiding introducer 10, the coronary sinus guiding introducer 10 returns to its predetermined shape as shown in FIG. 2.

The shape of the present invention allows an ordinarily skilled physician to canulate the coronary sinus in less than a minute, whereas canulation times for conventionally shaped introducers typically take up to almost an hour.

Figure 1A:
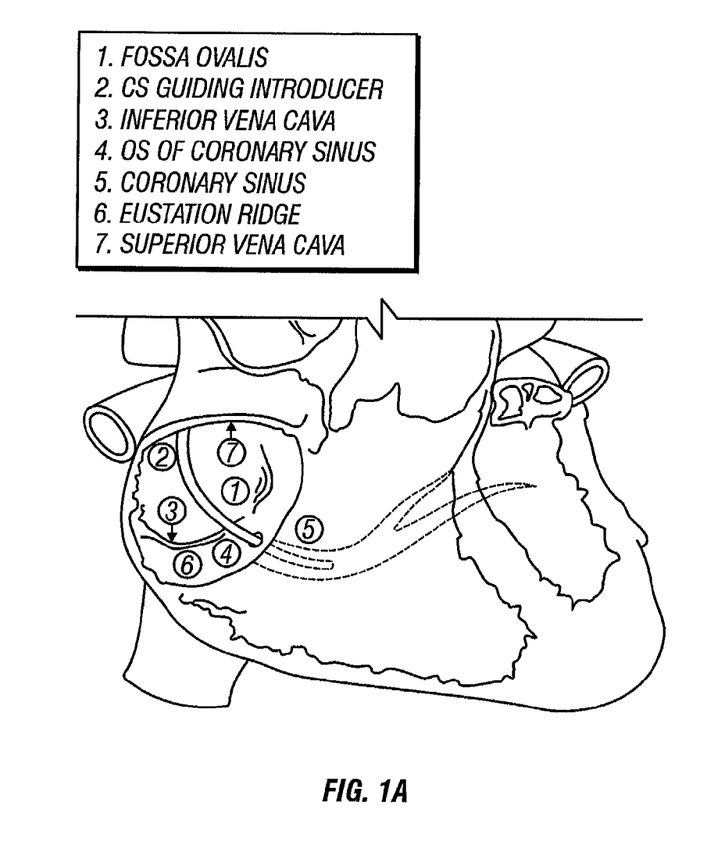
FIG. 1a is a cutaway view of the human heart from the right side showing the coronary sinus guiding introducer placed in the coronary sinus using the superior approach.
Figure 1B:
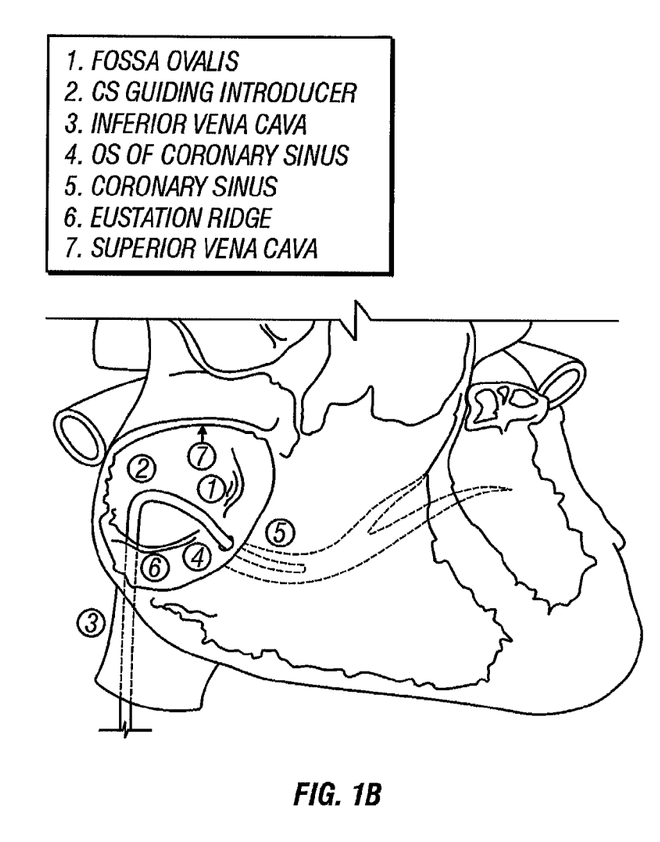
FIG. 1b is a cutaway view of the human heart showing an alternate preferred embodiment of the coronary sinus guiding introducer placed in the coronary sinus using an inferior approach.

In operation, a modified Seldinger technique is used for insertion of the coronary sinus guiding introducer 10 and any devices which will pass through the lumen of the guiding introducer 10 into the human body. Once the opening is provided in the vasculature, a guidewire is inserted and advanced through the vasculature into the chamber of the heart where the procedure will be performed. In a preferred embodiment of this invention using the superior approach to the right atrium, the guidewire is advanced through the left cephalic or left subclavian vein through the superior vena cava and into the right atrium. The guiding introducer 10 with dilator present in its lumen is then passed over the guidewire into the right atrium as shown in FIG. 1a.

The particular structure and curvature of the guiding introducer's distal portions 16 and 20 permits ease in locating the ostium of the coronary sinus in the superior approach. The tip of the coronary sinus guiding introducer 10 is then advanced as far as is required or desired into the coronary sinus. The dilator may be removed from the coronary sinus guiding introducer 10 at any point when appropriate. For example, if the dilator and the coronary sinus guiding introducer 10 both have the same shape, it may be best to introduce them in combination into the coronary sinus and only after the coronary sinus guiding introducer 10 is in place will the dilator be withdrawn. This may also be the preferred method of use when the dilator is precurved in the same shape as the preferred guiding introducer 10 as discussed in FIG. 2 and when a conventional straight introducer 10 is utilized. Alternatively, if the dilator is straight, it should be withdrawn from the precurved guiding introducer 10 prior to any attempt to place the guiding introducer 10 into the coronary sinus. If the dilator is precurved and the guiding introducer 10 is straight, the introducer 10 is advanced into the coronary sinus once the dilator has been advanced into the coronary sinus.

Once the guiding introducer 10 is in place in the coronary sinus, the medical device to be placed in the patient's heart is then advanced through the lumen of the guiding introducer 10 into the coronary sinus. For example, a temporary or permanent pacemaker lead may be advanced through the lumen of the guiding introducer 10 to be placed within the coronary sinus. A stylet may be inserted into the lumen of the lead to provide additional stiffness for the lead and to allow easy advancement of the lead through the lumen of the coronary sinus guiding introducer 10. The lead is then secured in place by conventional procedures. After the lead is in position, the guiding introducer 10 is withdrawn from the body of the patient. The order of removal of stylet and introducer 10 and securing the lead in place is not critical and may vary depending on the preference of the medical practitioner.

Because the proximal end of the lead is generally either attached to a connector or is directly attached to the pulse generator of the pacemaker, it is often critical that the guiding introducer 10 be splittable, sliceable or tearable to allow it to be separated into two lengthwise portions as it is removed from the patient's body. Once it is split, it can be removed from the operating theater. Alternatively, if the lead is relatively small and not connected to a pulse generator and the lumen of the guiding introducer 10 is relatively large, it will not be necessary for the introducer 10 to be splittable, sliceable or tearable.

The guiding introducer 10 can be used to introduce a number of different types of medical instruments into the body through its lumen including a permanent or temporary pacemaker lead, a defibrillator lead, ablation or sensing catheters or any such medical devices that will find use if placed within the coronary sinus. These other uses are well known in the industry and are within the contemplation of the present invention.

The guiding introducer 10 can also be used to introduce a wire guide into the coronary sinus. In this use, the guiding introducer 10 is first advanced into the coronary sinus followed by the guidewire. Once the guidewire is in place, the guiding introducer 10 can be removed. A lead or other types of medical devices can then be advanced over the wire guide until in place in the coronary sinus. In this case the lead, for example, may have a lumen or track so that it can be advanced using the guidewire into the coronary sinus.

Figure 3:
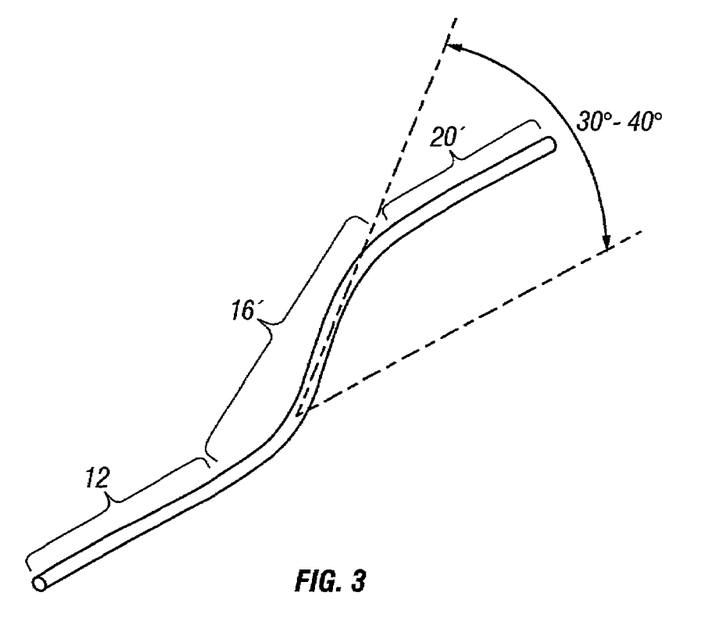
FIG. 3 is a perspective view of another embodiment where various portions of the introducer lie in different planes.

FIG. 3 illustrates another embodiment where various portions of introducer 10 lie in different planes. For example, proximal portion 12 may be defined to lie in a first plane, which can be called the basal plane in this description, although it is to be understood that proximal portion 12 is flexible and when in use will track the vasculature system's three dimensional shape. However, when introducer 10 is laid on a flat surface, proximal portion 12 will compliantly lie on that flat surface of the basal plane. Arcuate biased portion 16' will then be biased to lie in a plane making a dihedral angle of approximately 30-40° with respect to the basal plane. Similarly, distal-most end portion 20' will then be biased to lie in a plane making a dihedral angle of approximately 30-40° with respect to the arcuate biased portion 16'. The positive or negative angulation of the plane of distal-most end portion 20' is independent of the positive or negative angulation of the plane of arcuate biased portion 16'. Hence, distal-most end portion 20' may thus be either approximately parallel to the three dimensional orientation of the basal plane, may be approximately 60-80° even more inclined with respect to the basal plane, or may assume a virtually arbitrary angulation relative to the basal plane depending on the angulations chosen for the planes of distal-most end portion 20' and arcuate biased portion 16'. The out-of-plane angulations of the portions 12, 16' and 20' of introducer 10 may be chosen in any combination desired consistent with the teachings of the present invention.

Figure 4:
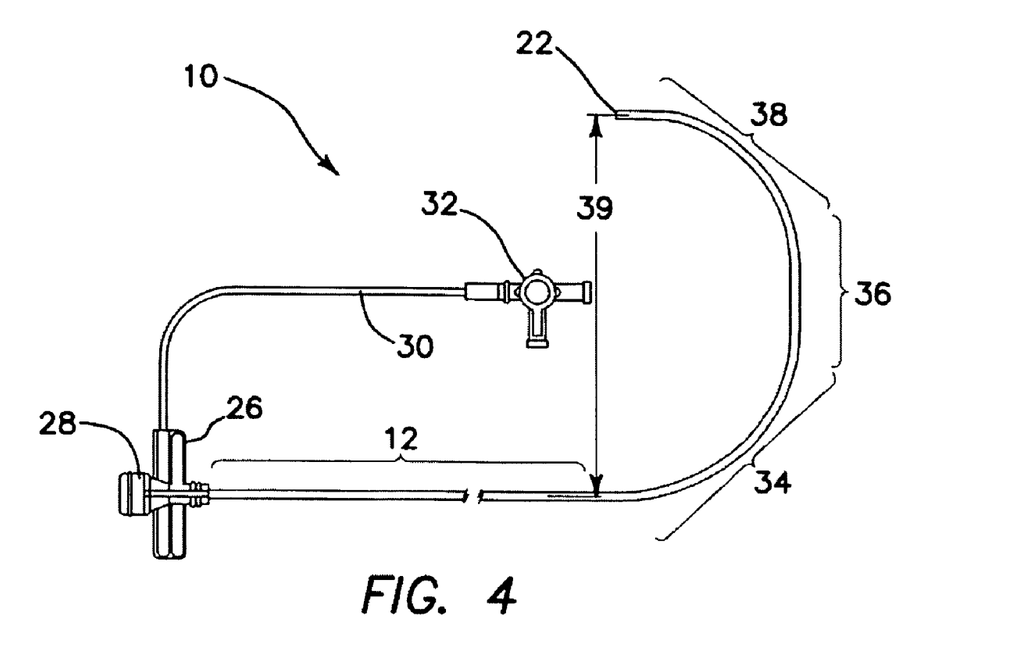
FIG. 4 is a plan view of another embodiment of an introducer formed according to the invention.

FIG. 4 is a plan view of an another embodiment of an introducer 10 which lies substantially in the plane of the drawing and which is adapted for use in the coronary sinus of the heart. A proximal handle 26 is connected to a hub 28. A flexible sidearm catheter 30 is communicated to hub 28 and is distally terminated with a hemostatic valve 32. A flexible body portion 12 extends to a first distal curved portion 34, which has a radius of curvature of approximately 2.5±0.25 inches. Curved portion 34 continues into a distal straight portion 36. Thereafter, introducer 10 continues distally with a second curved portion 38, which has a radius of curvature of approximately 2.0±0.25 inches and which bends in the same direction of first curved portion 34 making an approximate semicircular arc comprised of portions 34, 36 and 38. The chord 39 defined by a line extending across the entire arc, e.g. semicircular arc comprised of portions 34, 36 and 38 is approximately 5.125±0.25 inches when measured on a line drawn perpendicular to flexible portion 12. The entire length of introducer 10 from proximal handle 26 to distal tip 22 is approximately 13.78 inches (35 cm) and its diameter is 9 French. The length of portion 12 can of course be chosen arbitrarily according to design choice, the shape of the distal portion of introducer 10 being more materially important to proper placement in the coronary sinus.

Figure 5:
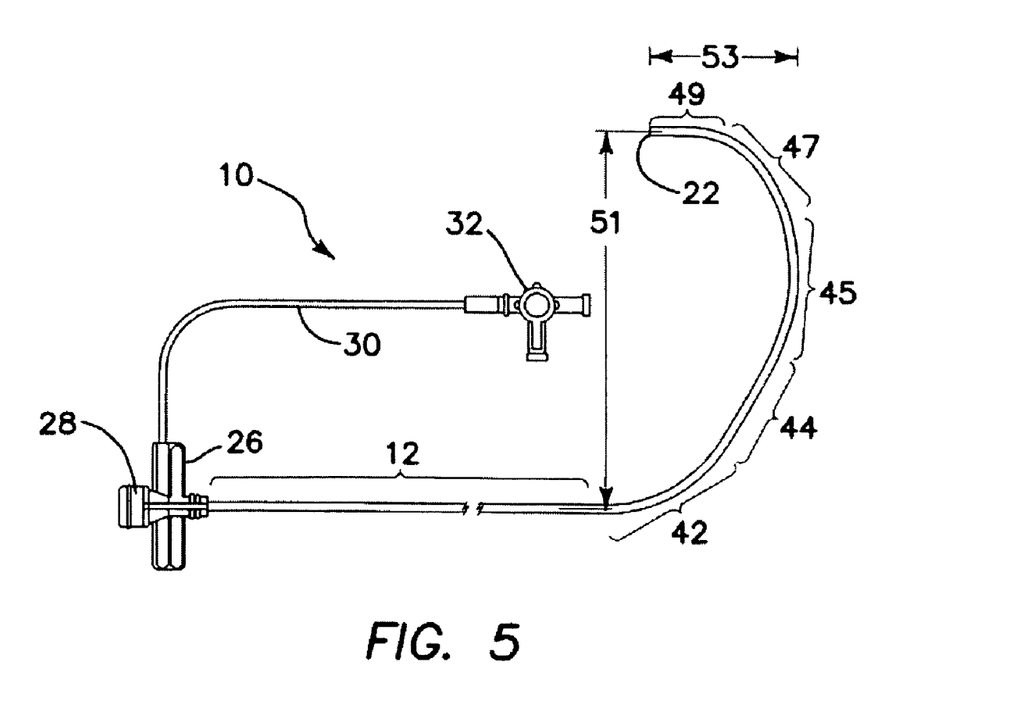
FIG. 5 is a plan view of still another embodiment of an introducer formed according to the invention.

The shape of FIG. 4 may be modified according to the invention to assume another embodiment as illustrated in the plan view of FIG. 5, which introducer 10 also lies substantially in the plane of the drawing and which is adapted for use in the coronary sinus of the heart. In this embodiment, flexible body portion 12 leads to a single curved portion 42, which has a radius of curvature of approximately 2.0±0.25 inches. Curved portion 42 continues distally in a straight portion 44. Straight portion 44 in turn continues with a second curved portion 45, which has a radius of curvature of approximately 2.75±0.25 inches. Second curved portion 45 transitions smoothly into a third curved portion 47, which has a radius of curvature of approximately 2.25±0.25 inches. Third curved portion 47 terminates with a straight portion 49 ending in distal tip 22. The centers of curvature of each of the first, second and third curved portions 42, 45 and 47 are on the same side of introducer 10 so that the distal end forms a compound arc having a chord 51 of approximately 5.46±0.25 inches in length when measured on a line drawn perpendicular to flexible portion 12. The longitudinal throw or length 53 of the distal most section of the compound arc measured from a line perpendicular to flexible portion 12 from the rearmost part of the compound arc to distal tip 22 is approximately 2.25±0.25 inches in length. The overall length of introducer 10 is about 17.71 inches (45 cm) and its diameter is 9 French. Again, the length of portion 12 can of course be chosen arbitrarily according to design choice, the shape of the distal portion of introducer 10 being more materially important to proper placement in the coronary sinus.

Figure 6:
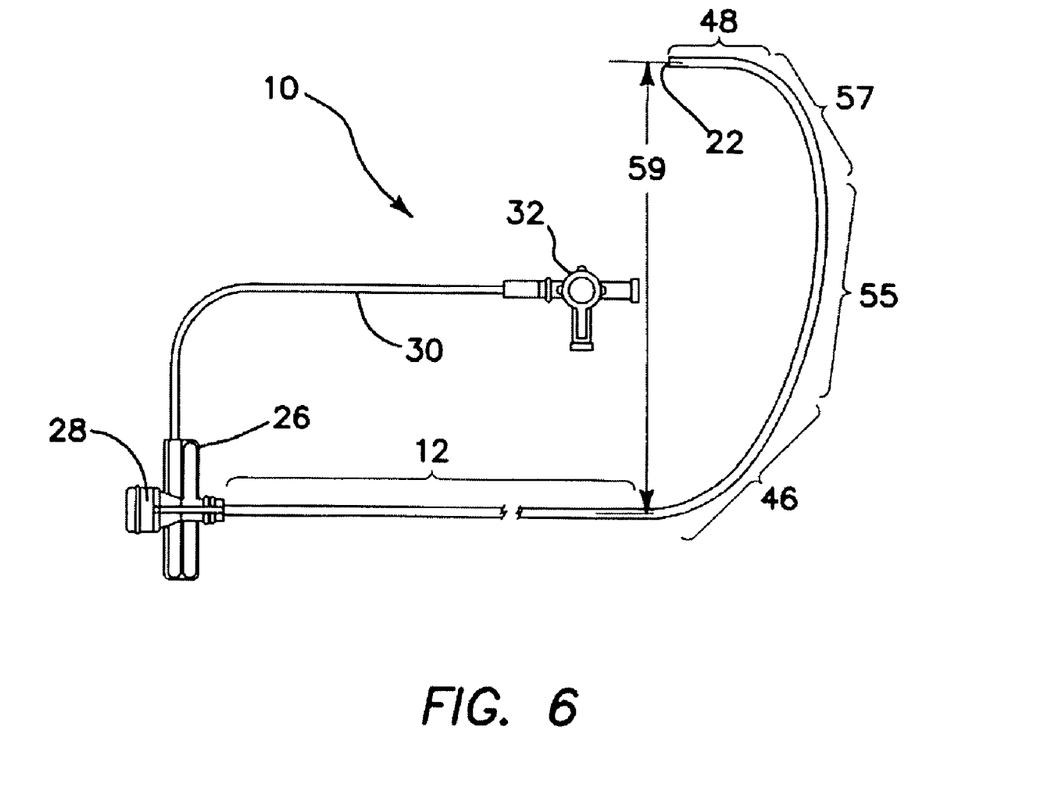
FIG. 6 is a plan view of yet another embodiment of an introducer formed according to the invention.

The shape of FIG. 5 may in turn be modified according to the invention to assume yet another embodiment as illustrated in the plan view of FIG. 6, which introducer 10 also lies substantially in the plane of the drawing and which is adapted for use in the coronary sinus of the heart. In this embodiment, flexible body portion 12 leads to a first curved portion 46, which curved portion 46 has a radius of curvature of approximately 2.0±0.25 inches. Curved portion 46 continues smoothly into a second curved portion 55, which has a radius of curvature of approximately 7.0±0.25 inches. Second curved portion 55 continues smoothly into a third curved portion 57, which has a radius of curvature of approximately 1.25±0.25 inches. Finally, third curved portion 57 continues distally in a straight portion 48 to distal tip 22. The centers of curvature of the curved portions 46, 55 and 57 all lie on the same side of introducer 10 so that a compound arc is formed defining a chord 59 having a length of approximately 6.5±0.25 inches when measured on a line drawn perpendicular to flexible portion 12. The overall length of introducer 10 is about 19.29 inches (49 cm) and its diameter is 9 French. Again, the length of portion 12 can of course be chosen arbitrarily according to design choice, the shape of the distal portion of introducer 10 being more materially important to proper placement in the coronary sinus.

Figure 7:
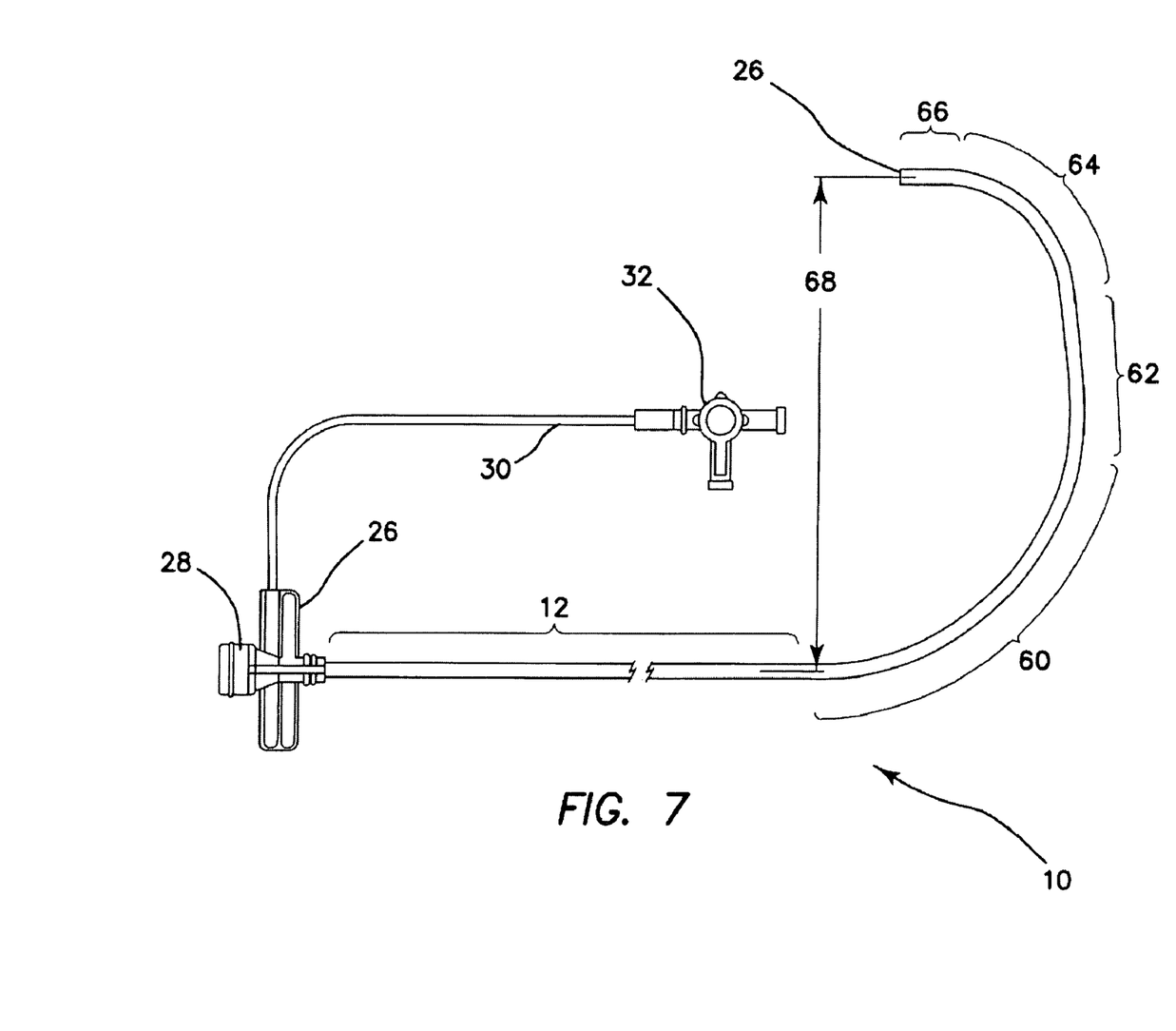
FIG. 7 is a plan view of another embodiment of an introducer formed according to the invention.
Figure 8:
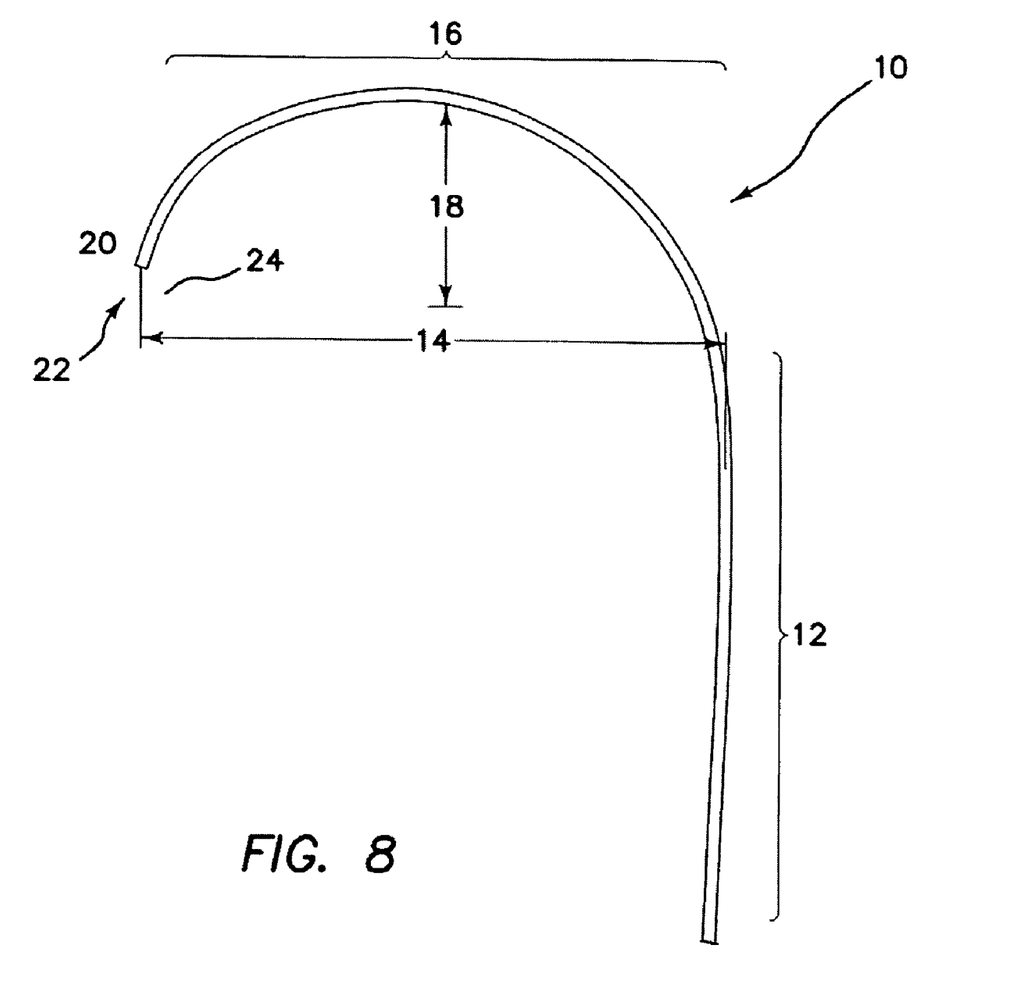
FIG. 8 is a side view of the embodiment of FIG. 2 where each subportion of the arc has the same curvature and the arc leads away from the proximal portion of the introducer.
Figure 9:
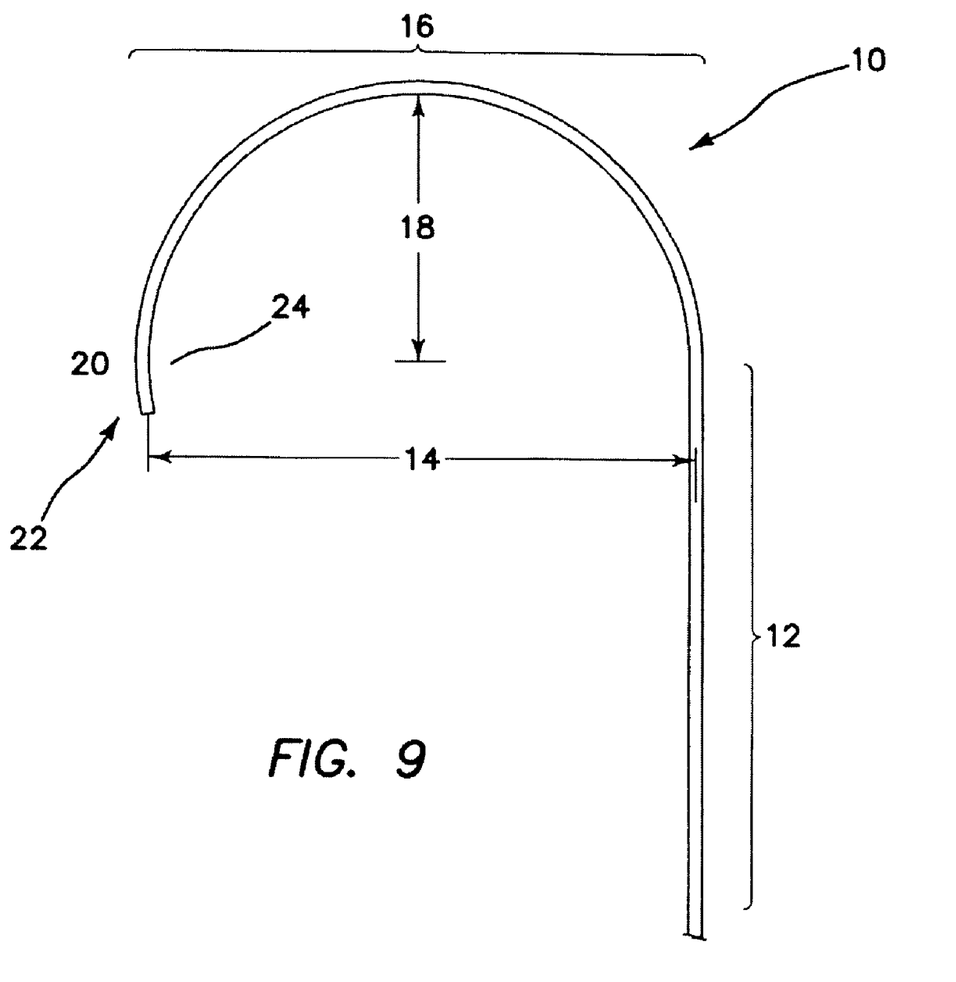
FIG. 9 is a side view of the embodiment of FIG. 2 where each subportion of the arc has the same curvature and the arc leads towards the proximal portion of the introducer.

The shape of FIG. 6 may in turn be modified according to the invention to assume yet another embodiment as illustrated in the plan view of FIG. 7, which introducer 10 also lies substantially in the plane of the drawing and which is adapted for use in the coronary sinus of the heart. In this embodiment, flexible body portion 12 leads to a first curved portion 60, which has a radius of curvature of approximately 2.875±0.25 inches. Curved portion 60 continues smoothly into a straight portion 62, which smoothly transitions to a second curved portion 64, which has a radius of curvature of approximately 1.25±0.25 inches. Second curved portion 64 continues smoothly into a straight portion 66 to distal tip 22. The centers of curvature of the curved portions 60 and 64 all lie on the same side of introducer 10 so that a compound arc is formed defining a chord 68 having a length of approximately 5.3±0.25 inches when measured on a line drawn perpendicular to flexible portion 12. The overall length of introducer 10 is about 17.17 inches (45 cm) and its diameter is 9 French. Again, the length of portion 12 can of course be chosen arbitrarily according to design choice, the shape of the distal portion of introducer 10 being more materially important to proper placement in the coronary sinus.

It may be appreciated that the curves shown in FIGS. 4-7 are each characterized by a proximal and distal curved portion forming part of the compound arc at the distal portion of introducer 10. The embodiments of FIGS. 5-7 are adapted for use in the coronary sinus of hearts of different topologies, e.g. child and adult. The embodiments of FIGS. 5 and 6 have the same radius of curvature for the proximal and distal curved portions, but differ in the nature of the curvatures of the interlying portions between the proximal and distal curved portions. The embodiments of FIGS. 5 and 6 can thus be thought of as having a similar shape, but in two different sizes, the size of FIG. 6 being the larger of the two. The embodiments of FIGS. 5 and 6 would thus be adapted for use in hearts of similar topology, but different sizes.

The invention is to be thus understood as fully scalable. For example, although the shapes of various embodiments are specified above, it is also to be expressly understood that these shapes may be scaled up or down from the illustrated embodiments given. For example, each of the recited dimensions may be specified as set forth above or increased or decreased by any percentage as may be desired according to the application at hand.

Guide catheter placement in the coronary sinus is essential for delivery of a biventricular pacing lead. The available delivery system shapes frequently cannot locate the coronary sinus without the use of an electrophysiology catheter. Therefore, designing a guide catheter that cannulates the coronary sinus easily, safely, and utilizing minimal contrast is imperative. In 31 cases, a standard multipurpose PTCA guiding catheter was hand-modified according to the invention to assume the shape of FIG. 2. The time and amount of contrast required to identify and engage the coronary sinus was recorded. Coronary sinus cannulation time was 5-202 seconds, mean cannulation time=31 seconds, median cannulation time=14 seconds. The amount of contrast required was less than 14.5 cc. The guide shape in case #30 was enlarged by 30% after 2 min 23 seconds, enabling cannulation to occur within 35 seconds. 31 cases were performed without complications and without the use of an electrophysiology catheter. The new shape developed in the invention provides safe, rapid access to the coronary sinus with minimal contrast usage and without the need for an electrophysiology catheter.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims.

For example, features of this guiding introducer 10 include its unique shape, but may also incorporate a splittable, sliceable or tearable structure, increased stiffness to minimize compression when positioned in tight bends, radioopaque tip markers, balloons and vents according to conventional design principles.

In a preferred embodiment the entire length of the guiding introducer 10 is splittable, sliceable or tear-away to permit the guiding introducer 10 to be divided into two separate halves as it is removed from the patient's body. Any structure which will permit the division of the guiding introducer 10 into two separate longitudinal halves is within the scope of the invention. In a preferred embodiment, the guiding introducer 10 contains a pair of mechanically formed, longitudinally extending zones of reduced thickness defined by internally scored, longitudinally shallow grooves or indentations running throughout the length of the introducer 10. These mechanically formed, reduced thickness zones permit the guiding introducer 10 to be "split" or "torn away" following use. Alternatively, if the lumen of the guiding introducer 10 is sufficiently large and the size of the diameter of the medical device passing through the guiding introducer 10 is not larger than the lumen of the guiding introducer 10, it is not necessary that the guiding introducer 10 be splittable, sliceable or tearable.

For example, notwithstanding the fact that the elements of a claim are set forth below in a certain combination, it must be expressly understood that the invention includes other combinations of fewer, more or different elements, which are disclosed in above even when not initially claimed in such combinations.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. A precurved coronary sinus guiding introducer for use in a dilated cardiomyopathic heart comprising:
    a flexible elongated member with a proximal and distal end, wherein the elongated member comprises a generally straight, proximal portion and a precurved distal portion, the proximal portion and distal portion formed to lie is a common plane,
    wherein the precurved distal portion comprises at least one curved proximal subportion and at least one curved or straight distal subportion, the precurved distal portion curving through a generally circular arc defined by a chord of predetermined length, and wherein the precurved distal portion has a predetermined height above the chord, and the curved or straight distal subportion being the distal most section of the precurved distal portion,
    wherein the distal most section of the precurved distal portion is generally oriented in a direction parallel to the straight, proximal portion;
    wherein the chord of the precurved distal portion has a length measured on a perpendicular to a longitudinal axis of the proximal portion between the beginning of the precurved distal portion where it meets the longitudinal axis of the proximal portion and a longitudinal axis of the opposing end of the precurved distal portion drawn parallel to the longitudinal axis of the proximal portion, and wherein the chord has the predetermined length of approximately 3.5 to 7 inches; wherein the predetermined height above the chord is approximately 1.5 inches to 4.0 inches, and
    wherein the curved or straight distal subportion is approximately 0.5 to 4.5 inches in length; and
    wherein the precurved distal portion has a minimal length of approximately 7.2 inches such that the distal end of the elongate member readily accesses the coronary sinus ostium in the dilated cardiomyopathic heart.

2. The coronary sinus guiding introducer of claim 1 further comprising a lumen extending through the member from the proximal to the distal end.

3. The coronary sinus guiding introducer of claim 1 wherein the chord has the predetermined length of approximately 4.6-7 inches.

4. The coronary sinus guiding introducer of claim 1 wherein the predetermined height above the chord is at least approximately 2.65 inches and a height from the distal tip to the precurved distal portion of at least 1.5 inches.

5. The coronary sinus guiding introducer of claim 1 wherein the curved or straight distal subportion is approximately 0.7-1.6 inches in length.

6. The introducer of claim 1 where the precurved distal portion includes one or more straight subportions.

7. The introducer of claim 6 where the precurved distal portion includes more than one arc.

8. The introducer of claim 6 where one of the straight subportions comprises a distal most straight subportion.

9. The introducer of claim 1 where the precurved distal subportion is comprised of two curved portions and two straight portions in alternating sequence with a distal one of the two straight portions leading to the distal end.

10. The introducer of claim 9 where the two curved portions comprise a proximal curved portion having a radius of curvature of approximately 2.0±0.25 to 2.85±0.25 inches and a distal curved portion having a radius of curvature of approximately 1.25±0.25 to 2.0±0.25 inches.

11. The introducer of claim 1 where the precurved distal subportion is further comprised of three curved portions and the curved or straight portion leading to the distal end, the three curved portions each having a different radius of curvature with the portion having the largest radius of curvature being between the other two curved portions.

12. The coronary sinus guiding introducer of claim 1 where the elongated member is separable.

13. The coronary sinus guiding introducer of claim 1 further comprising a sidearm catheter coupled to the elongated member.

14. The coronary sinus guiding introducer of claim 11 further comprising a radioopaque marker on the distal most section of the precurved distal portion.

15. The coronary sinus guiding introducer of claim 1 where the curved or straight distal subportion is parallel to the proximal portion.

16. A coronary sinus guiding introducer for use in a dilated cardiomyopathic heart, the introducer having a precurved shape comprising:
    a flexible elongated member with a proximal and distal end, wherein the elongated member comprises a generally straight, proximal portion and a precurved distal portion, the proximal portion and distal portion formed to lie in a common plane,
    wherein the precurved distal portion comprises at least one curved proximal subportion and at least one curved or straight distal subportion, the precurved distal portion curving through a generally circular arc defined by a chord of predetermined length and wherein the precurved distal portion has a predetermined height from the chord, and the curved or straight distal subportion being the distal most section of the precurved distal portion which is generally oriented in a direction parallel to the straight, proximal portion; and
    wherein the chord of the precurved distal portion has a length measured on a perpendicular to a longitudinal axis of the proximal portion between the beginning of the precurved distal portion where it meets the longitudinal axis of the proximal portion and a longitudinal axis of the opposing end of the precurved distal portion drawn parallel to the longitudinal axis of the proximal portion, and wherein the chord has a predetermined length of approximately 4.6 to 7 inches and height from the chord is approximately 2.5 to 4.0 inches, and wherein the precurved distal portion has a length of approximately 7.2 to 16 inches such that the distal end of the elongate member readily accesses the coronary sinus ostium in the dilated cardiomyopathic heart.

17. The coronary sinus guiding introducer of claim 16 where the elongated member is separable.

18. The coronary sinus guiding introducer of claim 16 further comprising a sidearm catheter coupled to the elongated member.

19. The coronary sinus guiding introducer of claim 16 further comprising a radioopaque marker on the distal most section of the precurved distal portion.

20. The coronary sinus guiding introducer of claim 16 where the distal most section of the precurved distal portion is parallel to the proximal portion.

21. A precurved coronary sinus guiding introducer with a distal end for use in a dilated cardiomyopathic heart comprising:

a proximal portion which is biased to be generally straight; and a precurved distal portion biased to curve through an arc defined by a chord of predetermined length and wherein the precurved distal portion has a predetermined height above the chord, the chord of the precurved distal portion has a length measured on a perpendicular to a longitudinal axis of the proximal portion between the beginning of the precurved distal portion where it meets the longitudinal axis of the proximal portion and a longitudinal axis of the opposing end of the precurved distal portion drawn parallel to the longitudinal axis of the proximal portion, and wherein the chord has the predetermined minimal length of approximately 3.5 inches, the predetermined minimal height above the chord is approximately 1.5 inches, and the precurved distal portion has a minimal length of approximately 6 inches, such that the distal end of the precurved distal portion of the introducer is generally oriented in a direction parallel to the straight, proximal portion and readily accesses the coronary sinus ostium in the dilated cardiomyopathic heart.

22. The introducer of claim 21 where the precurved distal portion includes one or more straight subportions 23. The introducer of claim 21 where the precurved distal portion includes more than one arc.

24. The introducer of claim 22 where one of the straight subportions comprises a distal most straight subportion.

25. The coronary sinus guiding introducer of claim 21 where the proximal portion and precurved distal portion are separable.

26. The coronary sinus guiding introducer of claim 21 further comprising a sidearm catheter coupled to the proximal portion.

27. The coronary sinus guiding introducer of claim 21 further comprising a radioopaque marker on the distal end of the precurved distal portion.

28. The coronary sinus guiding introducer of claim 21 where the distal end of the precurved distal portion is parallel to the proximal portion.

29. A precurved coronary sinus guiding introducer with a distal end for use in a dilated cardiomyopathic heart comprising:
    a flexible elongated member with a proximal and distal end, wherein the elongated member comprises
    a proximal portion biased to be generally straight, and
    a precurved distal portion biased to curve through an arc defined by a chord of predetermined length and wherein the precurved distal portion has a predetermined height above the chord, the chord of the precurved distal portion has a length measured on a perpendicular to a longitudinal axis of the proximal portion between the beginning of the precurved distal portion where it meets the longitudinal axis of the proximal portion and a longitudinal axis of the opposing end of the precurved distal portion drawn parallel to the longitudinal axis of the proximal portion, and wherein the chord has the predetermined length of approximately 3.5 to 7 inches, the predetermined height above the chord is approximately 1.5 inches to 4.0 inches such that the distal end of the introducer is generally oriented in a direction parallel to the straight, proximal portion and readily accesses the coronary sinus ostium in the dilated cardiomyopathic heart.

30. The introducer of claim 29 where the precurved distal portion includes one or more straight subportions.

31. The introducer of claim 30 where the precurved distal portion includes more than one arc.

32. The introducer of claim 31 where one of the straight subportions comprises a distal most straight subportion.

33. The introducer of claim 29 where the precurved distal portion has a length of approximately 5-16 inches.

34. The coronary sinus guiding introducer of claim 29 where the elongated member is separable.

35. The coronary sinus guiding introducer of claim 29 further comprising a sidearm catheter coupled to the elongated member.

36. The coronary sinus guiding introducer of claim 29 further comprising a radioopaque marker on the distal end of the introducer.

37. The coronary sinus guiding introducer of claim 29 where the distal end of the introducer is parallel to the proximal portion.

38. A precurved coronary sinus guiding introducer for use in a dilated cardiomyopathic heart comprising:
    a flexible elongated member with a proximal and distal end, wherein the elongated member comprises a generally straight, proximal portion which assumes a general direction and a precurved distal portion, the proximal portion and distal portion formed to lie is a common plane,
    wherein the precurved distal portion comprises at least one curved proximal subportion and at least one curved or straight distal subportion, the precurved distal portion curving through a generally circular arc defined by a chord of predetermined length and wherein the precurved distal portion has a predetermined height above the chord, and the curved or straight distal subportion being the distal most section of the precurved distal portion,
    wherein the chord of the precurved distal portion has a length measured on a perpendicular to a longitudinal axis of the proximal portion between the beginning of the precurved distal portion where it meets the longitudinal axis of the proximal portion and a longitudinal axis of the opposing end of the precurved distal portion drawn parallel to the longitudinal axis of the proximal portion, and wherein the chord has the predetermined length of approximately 3.5 to 7 inches,
    wherein the predetermined height above the chord is approximately 1.5 inches to 4.0 inches, and
    wherein the curved or straight distal subportion is approximately 0.5 to 4.5 inches in length and is oriented to extend in a direction approximating the general direction of the proximal portion; and
    wherein the precurved distal portion has a minimal length of approximately 7.2 inches such that the distal end of the elongate member readily accesses the coronary sinus ostium in the dilated cardiomyopathic heart.

39. The coronary sinus guiding introducer of claim 38 further comprising a lumen extending through the member from the proximal to the distal end.

40. The coronary sinus guiding introducer of claim 38 wherein the chord has the predetermined length of approximately 4.6-7 inches.

41. The coronary sinus guiding introducer of claim 38 wherein the predetermined height above the chord is at least approximately 2.65 inches and a height from the distal tip to the maximum extending portion of the precurved distal portion is at least 1.5 inches.

42. The coronary sinus guiding introducer of claim 38 wherein the curved or straight distal subportion is approximately 0.7-1.6 inches in length.

43. The introducer of claim 38 where the precurved distal portion includes one or more straight subportions.

44. The introducer of claim 43 where one of the straight subportions comprises a distal most straight subportion.

45. The coronary sinus guiding introducer of claim 38 where the elongated member is separable.

46. The coronary sinus guiding introducer of claim 38 further comprising a sidearm catheter coupled to the elongated member.

47. The coronary sinus guiding introducer of claim 38 further comprising a radioopaque marker on the distal most section of the precurved distal portion.

48. The coronary sinus guiding introducer of claim 38 where the curved or straight distal subportion is parallel to the proximal.

49. The introducer of claim 38 where the precurved distal portion includes more than one arc.

50. The introducer of claim 38 where the precurved distal subportion is comprised of two curved portions and two straight portions in alternating sequence with a distal one of the two straight portions leading to the distal end.

51. The introducer of claim 50 where the two curved portions comprise a proximal curved portion having a radius of curvature of 2.0±0.25 to 2.85±0.25 inches and a distal curved portion having a radius of curvature of 1.25±0.25 to 2.0±0.25 inches.

52. The introducer of claim 38 where the precurved distal subportion is further comprised of three curved portions and the curved or straight portion leading to the distal end, the three curved portions each having a different radius of curvature with the portion having the largest radius of curvature being between the other two curved portions.

53. A coronary sinus guiding introducer for use in a dilated cardiomyopathic heart, the introducer having a precurved shape comprising:
a flexible elongated member with a proximal and distal end, wherein the elongated member comprises a generally straight, proximal portion which assumes a general direction and a precurved distal portion, the proximal portion and distal portion formed to lie in a common plane,
wherein the precurved distal portion comprises at least one curved proximal subportion and at least one curved or straight distal subportion, the precurved distal portion curving through a generally circular arc defined by a chord of predetermined length and wherein the precurved distal portion has a predetermined height from the chord, and the curved or straight distal subportion being the distal most section of the precurved distal portion and being oriented to extend in a direction approximating the general direction of the proximal portion; and
wherein the chord of the precurved distal portion has a length measured on a perpendicular to a longitudinal axis of the proximal portion between the beginning of the precurved distal portion where it meets the longitudinal axis of the proximal portion and a longitudinal axis of the opposing end of the precurved distal portion drawn parallel to the longitudinal axis of the proximal portion. and wherein the chord has a predetermined length of approximately 4.6 to 7 inches and height from the chord is approximately 2.5 to 4.0 inches, and wherein the precurved distal portion has a length of approximately 7.2 to 16 inches such that the distal end of the elongate member readily accesses the coronary sinus ostium in the dilated cardiomyopathic heart.

54. The coronary sinus guiding introducer of claim 53 where the elongated member is separable.

55. The coronary sinus guiding introducer of claim 53 further comprising a sidearm catheter coupled to the elongated member.

56. The coronary sinus guiding introducer of claim 53 further comprising a radioopaque marker on the distal most section of the precurved distal portion.

57. The coronary sinus guiding introducer of claim 53 where the distal most section of the precurved distal portion is parallel to the proximal portion.

58. A precurved coronary sinus guiding introducer with a distal end for use in a dilated cardiomyopathic heart comprising:
a proximal portion which is biased to be generally straight and assumes a general direction, and
a precurved distal portion biased to curve through an arc defined by a chord of predetermined length and wherein the precurved distal portion has a predetermined height above the chord, the chord of the precurved distal portion has a length measured on a perpendicular to a longitudinal axis of the proximal portion between the beginning of the precurved distal portion where it meets the longitudinal axis of the proximal portion and a longitudinal axis of the opposing end of the precurved distal portion drawn parallel to the longitudinal axis of the proximal portion. and wherein the chord has the predetermined minimal length of approximately 3.5 inches, the predetermined minimal height above the chord is approximately 1.5 inches, and the precurved distal portion has a minimal length of approximately 6 inches, such that the distal end of the precurved distal portion of the introducer is oriented to extend in a direction approximating the direction of the proximal portion and readily accesses the coronary sinus ostium in the dilated cardiomyopathic heart.

59. The introducer of claim 58 where the precurved distal portion includes one or more straight subportions.

60. The introducer of claim 59 where the precurved distal portion includes more than one arc.

61. The introducer of claim 59 where one of the straight subportions comprises a distal most straight subportion.

62. The coronary sinus guiding introducer of claim 58 where the proximal portion and precurved distal portion are separable.

63. The coronary sinus guiding introducer of claim 58 further comprising a sidearm catheter coupled to the proximal portion.

64. The coronary sinus guiding introducer of claim 58 further comprising a radioopaque marker on the distal end of the precurved distal portion.

65. The coronary sinus guiding introducer of claim 58 where the distal end of the precurved distal portion is parallel to the proximal portion.

66. A precurved coronary sinus guiding introducer with a distal end for use in a dilated cardiomyopathic heart comprising:
a flexible elongated member with a proximal and distal end, wherein the elongated member comprises
a proximal portion biased to be generally straight and which assumes a general direction, and
a precurved distal portion biased to curve through an arc defined by a chord of predetermined length and wherein the precurved distal portion has a predetermined height above the chord, the chord of the precurved distal portion has a length measured on a perpendicular to a longitudinal axis of the proximal portion between the beginning of the precurved distal portion where it meets the longitudinal axis of the proximal portion and a longitudinal axis of the opposing end of the precurved distal portion drawn parallel to the longitudinal axis of the proximal portion, and wherein the chord has the predetermined length of approximately 3.5 to 7 inches, the predetermined height above the chord is approximately 1.5 inches to 4.0 inches such that the distal end of the introducer is oriented to extend in a direction approximating the general direction of the proximal portion and readily accesses the coronary sinus ostium in the dilated cardiomyopathic heart.

67. The introducer of claim 66 where the precurved distal portion includes one or more straight subportions.

68. The introducer of claim 67 where the precurved distal portion includes more than one arc.

69. The introducer of claim 67 where one of the straight subportions comprises a distal most straight subportion.

70. The introducer of claim 66 where the precurved distal portion has a length of approximately 5-16 inches.

71. The coronary sinus guiding introducer of claim 66 where the elongated member is separable.

72. The coronary sinus guiding introducer of claim 66 further comprising a sidearm catheter coupled to the elongated member.

73. The coronary sinus guiding introducer of claim 66 further comprising a radioopaque marker on the distal end of the introducer 74. The coronary sinus guiding introducer of claim 66 where the distal end of the introducer is parallel to the proximal portion.

75. A precurved coronary sinus guiding introducer for use in a dilated cardiomyopathic heart comprising:
a flexible elongated member with a proximal and distal end, wherein the elongated member comprises a generally straight, proximal portion and a precurved distal portion, the proximal portion and precurved distal portion formed to lie is a common plane, wherein the precurved distal portion comprises an arc or a combination of arcs and/or straight segments, the precurved distal portion defined by a chord of predetermined length and a predetermined height above the chord, the distal most section of the precurved distal portion being generally oriented in a direction parallel to the straight, proximal portion;
wherein the chord of the precurved distal portion has a length measured on a perpendicular to a longitudinal axis of the proximal portion between the beginning of the precurved distal portion where it meets the longitudinal axis of the proximal portion and a longitudinal axis of the opposing end of the precurved distal portion drawn parallel to the longitudinal axis of the proximal portion, and wherein the chord has the predetermined length of approximately 3.5 to 7 inches,
wherein the predetermined height above the chord is approximately 1.5 inches to 4.0 inches, and
wherein the precurved distal portion has a minimal length of approximately 7.2 inches such that the distal end of the elongate member readily accesses the coronary sinus ostium in the dilated cardiomyopathic heart.

76. The precurved coronary sinus guiding introducer of claim 75 where the distal most section of the precurved distal portion extends in a direction between 156° to 227° with respect to the proximal portion, where 180° is parallel to the proximal portion.

77. A precurved coronary sinus guiding introducer for use in a dilated cardiomyopathic heart comprising:
a flexible elongated member with a proximal and distal end, wherein the elongated member comprises a generally straight, proximal portion and a precurved distal portion, the proximal portion and precurved distal portion formed to lie is a common plane, wherein the precurved distal portion comprises an arc or a combination of arcs and/or straight segments, the precurved distal portion defined by a chord of predetermined length and a predetermined height above the chord, the distal most section of the precurved distal portion being generally oriented in a direction parallel to the straight, proximal portion: wherein the chord of the precurved distal portion has a length measured on a perpendicular to a longitudinal axis of the proximal portion between the beginning of the precurved distal portion where it meets the longitudinal axis of the proximal portion and a longitudinal axis of the opposing end of the precurved distal portion drawn parallel to the longitudinal axis of the proximal portion, and
wherein the chord has the predetermined length of approximately 3.5 to 7 inches,
wherein the predetermined height above the chord is approximately 1.5 inches to 4.0 inches, and
wherein the precurved distal portion has a minimal length of approximately 7.2 inches such that the distal end of the elongate member readily accesses the coronary sinus ostium in the dilated cardiomyopathic heart.

78. The precurved coronary sinus guiding introducer of claim 77 where the distal most section of the precurved distal portion extends in a direction between 156° to 227° with respect to the proximal portion, where 180° is parallel to the proximal portion.

* * * * *